(12) United States Patent
Armstrong et al.

(10) Patent No.: US 8,177,832 B2
(45) Date of Patent: May 15, 2012

(54) ENDOLUMINAL EXPANSION SYSTEM

(75) Inventors: Joseph R. Armstrong, Flagstaff, AZ (US); Edward H. Cully, Flagstaff, AZ (US); Craig T. Nordhausen, Flagstaff, AZ (US); Mark J. Ulm, Flagstaff, AZ (US); Michael J. Vonesh, Flagstaff, AZ (US)

(73) Assignee: W. L. Gore & Associates, Inc., Newark, DE (US)

( * ) Notice: Subject to any disclaimer, the term of this patent is extended or adjusted under 35 U.S.C. 154(b) by 0 days.

(21) Appl. No.: 12/876,779

(22) Filed: Sep. 7, 2010

(65) Prior Publication Data

US 2010/0331956 A1 Dec. 30, 2010

Related U.S. Application Data

(62) Division of application No. 11/407,426, filed on Apr. 19, 2006, now abandoned, which is a division of application No. 10/201,172, filed on Jul. 22, 2002, now abandoned.

(51) Int. Cl.
*A61F 2/82* (2006.01)

(52) U.S. Cl. ............................ 623/1.12; 623/1.11

(58) Field of Classification Search .......... 623/1.1–1.12, 623/1.15; *A61F 2/82*
See application file for complete search history.

(56) References Cited

U.S. PATENT DOCUMENTS

| | | |
|---|---|---|
| 3,585,707 A | 6/1971 | Stevens |
| 3,953,566 A | 4/1976 | Gore |
| 4,187,390 A | 2/1980 | Gore |
| 4,878,906 A | 11/1989 | Lindemann et al. |
| 5,019,085 A | 5/1991 | Hillstead |
| 5,026,377 A | 6/1991 | Burton et al. |
| 5,403,341 A | 4/1995 | Solar |
| 5,405,378 A | 4/1995 | Strecker |
| 5,571,169 A | 11/1996 | Plaia et al. |
| 5,690,643 A | 11/1997 | Wijay |
| 5,755,769 A | 5/1998 | Richard et al. |
| 5,797,879 A | 8/1998 | DeCampli |
| 5,814,405 A | 9/1998 | Branca et al. |

(Continued)

FOREIGN PATENT DOCUMENTS

EP 0732087 9/1996

(Continued)

*Primary Examiner* — Thomas J Sweet
*Assistant Examiner* — Jason-Dennis Stewart
(74) *Attorney, Agent, or Firm* — Wayne D. House

(57) ABSTRACT

An endoprosthesis expansion system having, in combination, a delivery component such as a length of catheter tubing having at its distal end an intermediate sheath component, and an inner tube within the full length of the delivery catheter and intermediate sheath component. The inner tube has a protrusion affixed to its distal end, and an expandable endoprosthesis is fitted in a compacted state about the intermediate sheath, immediately proximal to the protrusion. If the endoprosthesis is a self-expanding endoprosthesis (as is preferred), an exterior constraining sheath is required around the outer surface of the endoprosthesis. Following insertion of the endoprosthesis and delivery system into a body conduit (such as a blood vessel) and transport of the endoprosthesis to the desired site within the body conduit, the endoprosthesis is deployed by axially moving the protrusion against the system, thereby applying a radially directed outward force and causing simultaneous dilatation of the intermediate sheath and disruption of the exterior constraining sheath. Disruption of the exterior constraining sheath, in the case of a self-expanding prosthesis, releases the stored energy in the formerly constrained prosthesis, allowing it to expand and accomplish full deployment against the luminal surface of the body conduit at the desired site.

12 Claims, 7 Drawing Sheets

U.S. PATENT DOCUMENTS

| | | |
|---|---|---|
| 5,919,225 A | 7/1999 | Lau et al. |
| 5,971,990 A | 10/1999 | Venturelli |
| 6,019,787 A | 2/2000 | Richard et al. |
| 6,086,610 A | 7/2000 | Duerig et al. |
| 6,123,712 A | 9/2000 | Di Caprio et al. |
| 6,174,327 B1 | 1/2001 | Mertens et al. |
| 6,214,039 B1 | 4/2001 | Banas et al. |
| 6,224,627 B1 | 5/2001 | Armstrong et al. |
| 6,315,757 B1 | 11/2001 | Chee et al. |
| 6,355,060 B1 | 3/2002 | Lenker et al. |
| 6,383,212 B2 | 5/2002 | Durcan et al. |
| 6,432,129 B2 | 8/2002 | Di Caprio |
| 6,432,130 B1 | 8/2002 | Hanson |
| 6,447,540 B1 | 9/2002 | Fontaine et al. |
| 6,673,102 B1 * | 1/2004 | Vonesh et al. ............ 623/1.13 |
| 6,702,843 B1 * | 3/2004 | Brown et al. ............ 623/1.11 |
| 2001/0016726 A1 | 8/2001 | Dubrul et al. |
| 2002/0099432 A1 * | 7/2002 | Yee ............ 623/1.11 |
| 2002/0188341 A1 | 12/2002 | Elliott |

FOREIGN PATENT DOCUMENTS

| | | |
|---|---|---|
| EP | 0901776 | 3/1999 |
| EP | 1175875 | 1/2002 |
| WO | 93/17636 | 9/1993 |
| WO | 95/11055 | 4/1995 |
| WO | 98/20812 | 5/1998 |
| WO | 98/27894 | 7/1998 |

* cited by examiner

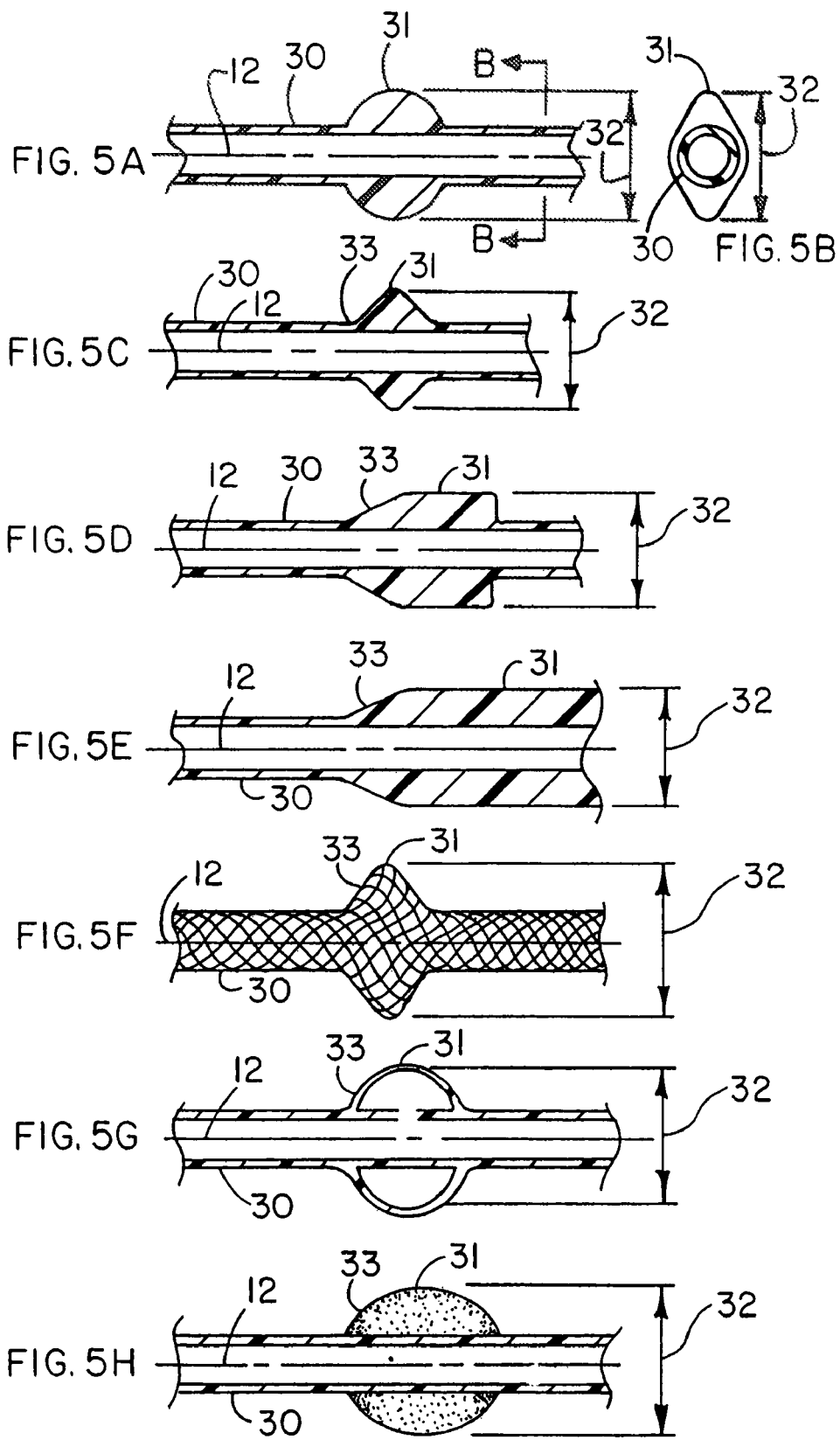

ENDOLUMINAL EXPANSION SYSTEM

CROSS REFERENCE TO RELATED APPLICATIONS

This application is a divisional of application Ser. No. 11/407,426 filed Apr. 19, 2006 now abandoned, which is a divisional of application Ser. No. 10/201,172, filed Jul. 22, 2002 (now abandoned).

FIELD OF THE INVENTION

The present invention relates to the transcatheter delivery and remote deployment of implantable medical devices and more particularly to a system for the expansion and deployment of endoprostheses.

BACKGROUND OF THE INVENTION

Endoluminal therapies typically involve the insertion of a delivery catheter that transports an implantable prosthetic device into a body conduit through a small, often percutaneous, remote access site. Once access to the body conduit is achieved, the delivery catheter is used to mediate intraluminal delivery and subsequent deployment of the prosthesis via one of several techniques. In this fashion, the prosthesis can be remotely implanted to achieve a therapeutic outcome. In contrast to conventional surgical therapies, endoluminal treatments are distinguished by their "minimally invasive" nature.

Self-expanding endoprostheses are generally comprised of a stent component with or without a graft covering over the stent interstices. They are designed to spontaneous dilate (i.e., elastically recover) from their delivery diameter, through a range of intermediary diameters, up to a maximal, pre-determined functional diameter. The endoluminal delivery and deployment of self-expanding endoprostheses pose several unique problems. First, the endoprosthesis itself must be radially compacted to a suitable introductory size (or delivery diameter) to allow insertion into the vasculature, then it must be constrained in that compacted state and mounted onto a delivery device such as a catheter shaft. Subsequently, the constraint must be removed in order to allow the endoprosthesis to expand to its functional diameter and achieve the desired therapeutic outcome. Preferably, the means of constraint will not adversely affect the delivery catheter performance (e.g., detracting from the flexibility of the delivery system) or add significantly to introductory profile. The constraint must also incorporate some type of release mechanism or scheme that can be remotely actuated by the implanting clinician. Consequently, deployment methodologies that are consistent with conventional interventional practices are preferred.

Delivery mechanisms for self-expanding endoprostheses of the prior art may be generally classified into one of two general categories, either coaxial sheaths or fiber-based constraints. Delivery systems also exist that use both of these types of mechanisms in combination.

Tubular coaxial sheaths are one approach used to constrain the compacted self-expanding endoprosthesis. Normally, these coaxial sheaths extend over the entire length of an inner delivery catheter onto which the endoprosthesis is mounted near the catheter tip (i.e., leading end). Deployment is typically initiated by pulling on a handle or knob located near the hub (i.e., trailing end) of the catheter, which retracts the constraining sheath and allows the device to expand. During this procedure, the clinician maintains the position of the device by holding the inner (delivery) catheter in a stationary position. Existing problems and/or complications with the tubular coaxial sheath type of delivery system include friction between compacted device and constraining sheath, friction between the constraining sheath and delivery catheter, and friction between the delivery catheter and constraining sheath hemostasis valve, all of which can hinder deployment accuracy, speed and control. Additionally, a tubular coaxial constraining sheath can also reduce flexibility and add introductory profile due to the thickness of the constraining sheath.

In the fiber-based delivery systems, the self-expanding endoprosthesis is constrained in the delivery profile by one or more removable fibrous strands, with or without an additional implantable constraint element. The endoprosthesis is released from its compacted state through tension applied to a deployment "cord" that normally runs through an additional lumen within the delivery catheter. Typically, applying tension to the deployment cord initiates the release of the fiber constraint by, for example, unlacing linear slip knots (see Lau, et al., U.S. Pat. No. 5,919,225), removing circumferential croquet knots (e.g., Strecker, U.S. Pat. No. 5,405,378), or detaching the interlocking loops of a warp-knitted constraint (e.g., Armstrong et al., U.S. Pat. No. 6,224,627). Other fiber-based delivery systems are described by Lindemann, U.S. Pat. No. 4,878,906, and Hillstead, U.S. Pat. No. 5,019,085.

Another variant of the fiber-based delivery systems is the mechanism employed in the EXCLUDER® endoprosthesis marketed by W.L. Gore and Associates, Inc (Flagstaff, Ariz.). This mechanism entails a "chain-stitch" sewn into the seam of a biocompatible constraining tube that contains the compacted endoprosthesis. Applying tension to the fibrous constraint in this mechanism allows the seam in the biocompatible constraining tube to be open, and the self-expanding endoprosthesis to deploy. The biocompatible constraining tube is implanted along with the endoprosthesis, trapped between the abluminal surface of the device and the wall of the host vessel. See WO98/27894.

Problems with fiber-based type of delivery systems include possible premature deployment during introduction to the vascular system through hemostasis valves, extra lumens required on the delivery catheter which can increase profile, possible snagging of fiber(s) on the compacted implantable device, the possibility of emboli resulting from moving lines between the catheter and the blood vessel, and possible breakage of the deployment cord itself.

U.S. Pat. Nos. 5,755,769 and 6,019,787 to Richard et al. teach another constraining sheath around a self-expanding stent. The sheath is cut longitudinally into several segments by cutting wires or fibers actuated by pulling a handle at the opposite end of the delivery system. The sheath is attached to or integral to the delivery catheter with the result that the segments are removed with the catheter following stent deployment. No catheter balloon or other means for exerting a circumferential disrupting force to the sheath is suggested, nor are materials appropriate for the sheath suggested. This design requires lines to run over the length of the catheter.

U.S. Pat. No. 6,086,610 to Duerig et al. teaches a self-expanding stent provided with a tubular constraining sheath that is plastically deformable by a circumferential distending force such as a catheter balloon. This sheath remains implanted with the stent following deployment and fully covers the entire circumference of the stent in the fashion of a conventional stent covering, i.e., the tubular sheath is not disrupted. The Duerig et al. device is delivered from a conventional balloon catheter, but thought to have limitations, including radial recoil of the sheath after the balloon is pressurized and deflated, which can compromise luminal gain. Further, the presence of the cover may adversely affect the ability of the stent to fully deploy, and the balloon length must be equal to or longer than the stent, and this long balloon can potentially damage the vessel.

SUMMARY OF THE INVENTION

The present invention relates to an endoprosthesis expansion system comprising, in combination, a delivery component such as a length of catheter tubing having at its distal end an intermediate sheath component, and an inner elongate actuation member that is preferably an inner tube located within the full length of the delivery catheter and intermediate sheath component. The inner elongate actuation member (e.g., inner tube) has a protrusion affixed to its distal end, and an expandable endoprosthesis is fitted in a compacted state about the intermediate sheath, proximal to the protrusion. If the endoprosthesis is a self-expanding endoprosthesis (as is preferred), an exterior constraining sheath is required around the outer surface of the endoprosthesis to contain the endoprosthesis in a compacted configuration. Following insertion of the endoprosthesis and delivery system into a body conduit (such as a blood vessel) and transport of the endoprosthesis to the desired site within the body conduit, the endoprosthesis is deployed by axially moving the protrusion through the system, thereby applying a radially directed outward force and causing simultaneous dilatation of the intermediate sheath and disruption of the exterior constraining sheath. Alternatively, axial movement of the elongate actuation member against the end of the intermediate sheath, applying axial compression to the intermediate sheath, may cause the intermediate sheath to shorten and simultaneously increase in diameter, thereby initiating expansion and deployment of the endoprosthesis. Disruption of the exterior constraining sheath, in the case of a self-expanding prosthesis, releases the stored energy in the formerly constrained prosthesis, allowing it to spontaneously expand and accomplish full deployment against the luminal surface of the body conduit at the desired site.

The exterior constraining sheath is preferably made of an implantable material and may be left captured between the endoprosthesis and the luminal surface of the body conduit. Alternatively, the exterior constraining sheath may be secured to the adjacent delivery catheter and withdrawn from between the endoprosthesis and the wall of the body conduit when the delivery catheter is withdrawn.

If a non-self-expanding endoprosthesis is used (e.g., a balloon-expandable stent), diametrical expansion may be accomplished by moving the protrusion axially through the stent, thereby enlarging the diameter by plastically deforming the stent. Likewise, as described with the self-expanding stent embodiment, the application of axial compression against one end of the intermediate sheath by the protrusion can cause an increase in the diameter of the intermediate sheath, forcing a corresponding diametrical increase in the balloon expandable stent.

In addition to stent devices, the endoprostheses utilized with the present invention may also be stent-grafts. The phrase "stent-graft" is used herein to describe a stent provided with a covering, typically of a vascular graft material such as porous expanded polytetrafluoroethylene (ePTFE) or polyethylene terephthalate (PET). The covering may be provided over either or both of the inner and outer surfaces of the stent. The covering may cover a portion of the otherwise open stent interstices or it may cover all of the stent interstices.

While the system of the present invention is intended primarily for stents and stent-grafts for use in vascular repairs, it is also useful for expandable devices for other applications in other body conduits, e.g., esophageal or biliary duct repairs.

While a protrusion can be used to initiate deployment without an intermediate sheath inside the endoprosthesis, the use of the intermediate sheath, made from a thin, strong and lubricious material, prevents the protrusion from damaging the endoprosthesis (particularly if the endoprosthesis is a stent-graft with a covering on the luminal surface). It also reduces the likelihood of "bunching" of the endoprosthesis due to the application of an axial force. It can likewise reduce the amount of axial force required as well as reducing the variability of the axial force (as the protrusion moves along the internal length of the endoprosthesis), by providing a uniform compression resistance against the protrusion as opposed to the variable resistance provided by the wire surface of the interior of an endoprosthesis.

Both the exterior constraining sheath and the intermediate sheath may be made to be dilatable or disruptable by various and similar means. For the exterior constraining sheath, it is preferred to provide a line of perforations partially or entirely through the wall of the tubular constraining sheath, parallel to the longitudinal axis of the tubular constraining sheath. The constraining sheath may be caused to disrupt by splitting along this line of perforations, upon the application of an outwardly directed radial force from within the sheath (and within the contained endoprosthesis).

For the intermediate sheath located within the endoprosthesis, it is preferred that it is of a substantially tubular form and is dilatable via one or more, equally radially-spaced apart splits are used along the length of that sheath. Alternatively, the intermediate sheath may be elastically or plastically deformable by the protrusion. In other alternatives, the intermediate sheath may be caused to be split, ripped, torn or otherwise changed in proportion by the movement of the protrusion against and/or through the intermediate sheath. Any of these mechanisms are considered to constitute dilatation of the intermediate sheath. It is apparent that the tubular form of the intermediate sheath includes various embodiments and as such is considered to be a substantially tubular sheath.

The present invention also provides a means of controlling the radial dynamics of device deployment. For example, the present invention can be configured to 'pop' open to allow rapid device deployment, or alternatively to undergo more gradual, controlled, stepwise release during device deployment, or a combination of both.

The constraining sheath may be imbibed with various pharmaceutical, biological, or genetic therapies for targeted luminal delivery of these substances. Following deployment of the endoprosthesis, these therapeutic agents can be released over time. An advantage of this approach is that the loading of the sheath with any of these therapeutic agents can be performed independent of the endoprosthesis manufacture. Further, radiopaque elements may be incorporated into the constraining sheath (or other system components, notably the catheter tubes) to facilitate fluoroscopic visualization.

The present invention may also be used to deliver and deploy multiple devices positioned in sequential order on the delivery catheter.

In a preferred embodiment, the constraining sheath can be made to be extremely thin, or "delicate," for minimal implantation profile. Such a delicate constraining sheath is not adequate, without further exterior support, to constrain the endoprosthesis assembly (particularly when the assembly includes a self-expanding endoprosthesis) for very long periods of time or for shorter periods when exposed to elevated temperatures. The use of such a delicate constraining sheath is made practically possible when the assembly is provided with an additional tubular packaging sheath that prevents inadvertent disruption of the constraining sheath or undesirable increase in diameter of the assembly (e.g., in an amount of 0.15 mm or more). The tubular packaging sheath, fitted coaxially about the exterior of the "delicate" constraining sheath, is removed prior to implantation and accordingly is not required to be made of an implantable material or a material with a thin wall. Alternatively, the endoprosthesis assembly may incorporate such a delicate constraining sheath without the use of a packaging sheath if it is stored at reduced temperatures, such as 5° C. or less, prior to implantation.

BRIEF DESCRIPTION OF THE DRAWINGS

FIGS. 5A and 5C-5H are longitudinal cross-sections of the inner tube and protrusion, describing various embodiments of the protrusion.

FIG. 5B is a transverse cross-sectional view taken at section B-B of FIG. 5A of the protrusion of FIG. 1, describing an embodiment wherein the transverse cross-section of the protrusion is not round.

DETAILED DESCRIPTION OF THE INVENTION

Figure 1:
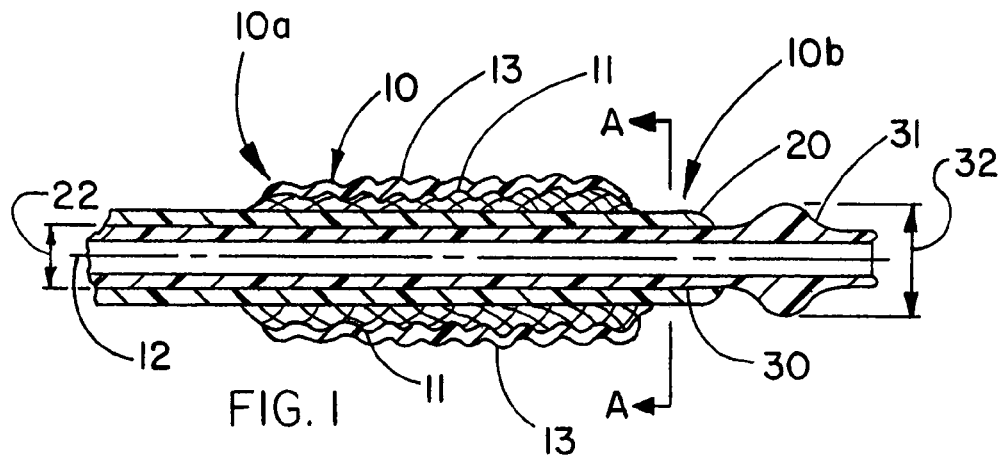
FIG. 1 is a longitudinal cross section of a compacted and constrained endoprosthesis mounted on an intermediate sheath, which is mounted upon an inner tube incorporating a protrusion at the distal end that, when moved axially through or against the intermediate sheath and endoprosthesis, applies a force directed radially outward to initiate deployment of the endoprosthesis.

FIG. 1 is a longitudinal cross section of the endoprosthesis expansion system 10 of the present invention. The system 10 has a proximal end 10*a* and a distal end 10*b*, wherein proximal end 10*a* is considered to be the end from which a delivery catheter extends to a site at which the system was originally inserted into a body conduit. Endoprosthesis 11 is indicative of any type of endoluminal medical device which might be usefully contained at a smaller diameter for insertion into a body conduit and subsequently deployed to a larger diameter at a desired location within the body conduit. The endoprosthesis is preferably a self-expanding device, and is most preferably a stent of the self-expanding type. While these stents are most commonly used for repair of the vasculature (e.g., repair of stenoses or aneurysmal repair), they are also used for other applications in other body conduits (e.g., esophageal or bile duct repairs). These self-expanding stents are typically of nitinol wire although other materials may be used, e.g., stainless steels or polymeric materials including resorbable polymers.

Alternatively, some balloon expandable devices may be expanded with the present inventive system, without requiring an exterior constraining sheath as do self-expanding devices.

According to the present invention, a self expanding device in use as a part of the present endoprosthesis expansion system is provided with an exterior constraining sheath to retain the self-expanding endoprosthesis at its small, compacted diameter at which it is intended to be inserted into a body conduit for subsequent expansion and deployment. The constraining sheath is disrupted by activation of the expansion and deployment mechanism of the present invention. The constraining sheath is preferably made from an implantable material, most preferably a tube of porous expanded PTFE (hereinafter ePTFE), made generally as taught by U.S. Pat. Nos. 3,953,566 and 4,187,390 to Gore. The tube is most preferably provided with a line of perforations through the wall, parallel to the length of the tube. The line of perforations provides a yield point along which the constraining sheath will disrupt by splitting. Forcibly expanding the endoprosthesis in a radially outward direction, using force applied from within the lumen of the endoprosthesis, causes the perforation line to disrupt, initiating expansion and deployment of the self-expanding endoprosthesis. The disrupted, now-split constraining sheath, being of an implantable material such as ePTFE, preferably remains implanted with the deployed endoprosthesis, held captive between the endoprosthesis and the wall of the body conduit at the site of deployment. As such, the implantable constraining sheath may optionally be attached to the exterior surface of the self-expanding stent, preferably along an axially-oriented line that is 180° opposite the line of perforations. Alternatively, the constraining sheath can be configured to be removable following deployment of the endoprosthesis, by having previously secured it to a component of the delivery system such as a catheter shaft and withdrawing it from between the endoprosthesis and the wall of the body conduit when the catheter is withdrawn.

The endoprosthesis may be a stent-graft having a stent component and a covering over some or all of the open interstices of the stent. The covering may be provided over either or both of the inner and outer surfaces of the stent. It is preferably ePTFE, and can be attached to the stent by any of various means known in the art. Any such stent covering is in addition to and preferably separate from the constraining sheath used with a self-expanding endoprosthesis.

FIG. 1 shows a compacted and constrained endoprosthesis 11 mounted on an intermediate sheath 20, which is in turn mounted upon inner tube 30. As a self-expanding endoprosthesis is described by the figures, it is shown with a constraining sheath 13 about its exterior surface. Constraining sheath 13, as will be described, is disruptable to allow for expansion and deployment of endoprosthesis 11 at a desired site within a body conduit.

Inner tube 30 possesses at its distal end a protrusion 31 having a maximum diameter 32 (taken perpendicular to the longitudinal axis 12 of the system 10) that is larger than the inner diameter 22 of intermediate sheath 20 (also taken perpendicular to longitudinal axis 12). Intermediate sheath 20 is preferably an extension of a delivery catheter extending beyond the insertion site at which endoprosthesis and associated delivery system entered the body conduit. Intermediate sheath 20 is preferably made from a thin, strong and lubricious polymeric material such as PET. Intermediate sheath 20 is preferably as thin or thinner than about 0.12 mm. In one alternative, the intermediate sheath may be an integral part of the delivery catheter tube.

Most preferably, inner tube 30 comprises a composite tube having an inner PTFE lining 24 of about 0.03 mm thickness, and an outer jacket 25 of polyamide, about 0.18 mm thick, having a braided stainless steel wire reinforcement (24 picks/cm, rectangular cross section wire 0.01×0.07 mm, Fluorotek, Easton Pa.) embedded in the wall of the jacket 25.

Protrusion 31 is preferably a separate component, also of polyamide, that is melt-bonded to the exterior surface of the inner tube at a desired location at one end of a length of the inner tube. Melt bonding is accomplished by placing a mandrel inside inner tube 30, fitting the protrusion 31 over the inner tube 30, fitting a short length of fluorinated ethylene propylene shrink tubing over the protrusion 31, and heating the assembly above the melt temperature of polyamide thereby causing simultaneous shrinking of the shrink-tubing. After heating, the shrink tubing is carefully removed with the aid of a scalpel blade, taking care not to damage the exterior surface of the protrusion 31 or the polyamide tubing 30. Finally, the mandrel is removed from within the tube. Multiple melt steps may be required to adequately increase the protrusion diameter to the extent desired.

Figure 2A:
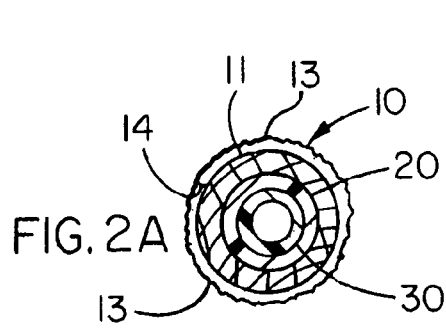
FIG. 2A is a transverse cross sectional view taken at section A-A of FIG. 1.

FIG. 2A is a transverse cross sectional view taken at section A-A of FIG. 1 wherein the intermediate sheath 20 is diametrically distensible when compressed axially and distended diametrically when protrusion 31 is moved axially against one end of the intermediate sheath or through its lumen. Endoprosthesis 11, in this instance a self-expanding endoprosthesis, is shown enclosed by constraining sheath 13. Constraining sheath 13 is provided with a line of perforations 14 that extends for the length of the constraining sheath 13, enabling it to subsequently disrupt along this split line 14 when the endoprosthesis is deployed.

While it is possible to initiate expansion and deployment of a constrained, self-expanding endoprosthesis without the use of intermediate sheath 20, the use of this additional component has been found to aid in the practical expansion of an endoprosthesis via axial movement of a protrusion 31 against the end of the intermediate sheath 20 or through the center of the intermediate sheath 20 and endoprosthesis 11. Without the intermediate sheath 20, the direct contact of the protrusion 31 against the inner surface of the endoprosthesis 11 may result in bunching up of the prosthesis axially and possible damage to the endoprosthesis, particularly if it is a stent-graft with a covering on the luminal surface of the stent that is vulnerable to damage from the protrusion 31. The use of intermediate sheath 20 provides for more uniform axial compression resistance against the force exerted by the protrusion 31, thereby improving uniformity of the expansion and deployment of the endoprosthesis. Likewise, the use of a lubricious material such as PET for the intermediate sheath 20 aids in reducing and improving the uniformity of the axial effort that must be applied via a guidewire and/or catheter shaft to cause expansion and deployment of endoprosthesis 11.

Figure 2B:
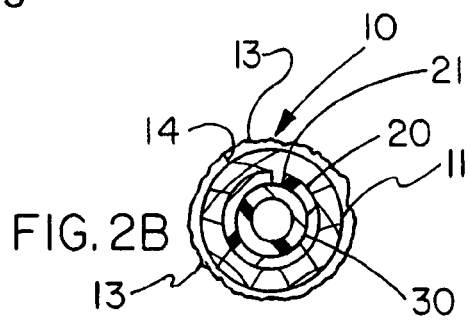
FIG. 2B is a transverse cross sectional view taken at section A-A of FIG. 1 wherein, in an alternative embodiment, the intermediate sheath is split in one place, allowing it to enlarge diametrically when the protrusion of FIG. 1 is passed through it or applies compression against the end of the intermediate sheath.

FIG. 2B is a transverse cross sectional view taken at section A-A of FIG. 1 showing an alternative embodiment of intermediate sheath 20 wherein the intermediate sheath 20 is provided with a longitudinally-oriented split 21 in one place, in a direction parallel to longitudinal axis 12, allowing it to enlarge when the protrusion 31 applies axial compression against one end or is passed through it. While the intermediate sheath 20 is most preferably split entirely through its thickness, it may also be split through only a portion of the thickness if the remaining unsplit thickness will yield reliably when the protrusion 31 is forcibly pulled through the center of the intermediate sheath 20.

Figure 2C:
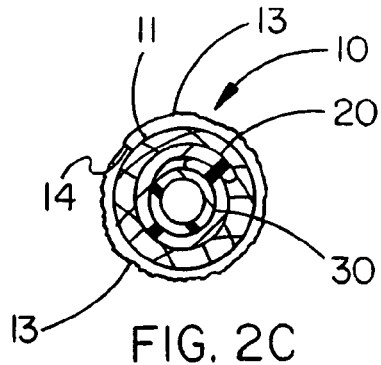
FIG. 2C is a transverse cross sectional view taken at section A-A of FIG. 1 wherein, in another alternative, the intermediate sheath is split and coiled upon itself (in jelly-roll fashion).

FIG. 2C is a transverse cross sectional view taken at the same location with respect to FIG. 1, showing another alternative embodiment of sheath 20 wherein sheath 20 is coiled upon itself (in jelly-roll fashion), thereby allowing it to enlarge when the protrusion 31 is passed through it or applies axial compression against one end.

Figure 2D:
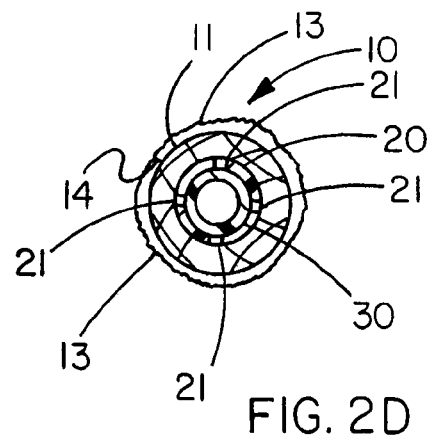
FIG. 2D is a transverse cross sectional view taken at section A-A of FIG. 1 wherein, in another alternative, the intermediate sheath is split in several places.

FIG. 2D is a transverse cross sectional view taken at section A-A of FIG. 1 wherein the intermediate sheath 20 is provided with multiple splits 21 in several places, thereby enabling it to expand when the protrusion of FIG. 1 is passed through it or applies axial compression against one end.

Figure 2E:
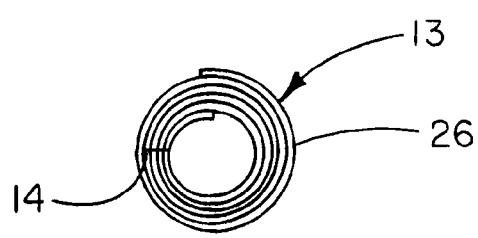
FIG. 2E is a transverse cross section of a preferred constraining sheath construction.

FIG. 2E is a transverse cross section describing a preferred construction of a constraining sheath 13 for use around the exterior surfaces of a self-expanding endoprosthesis 11. Constraining sheath 13 comprises a wrap of a thin ePTFE film 26, made as taught by U.S. Pat. No. 5,814,405 to Branca et al. The particular ePTFE film used has a bulk density of about 0.25 g/cc and is provided with a discontinuous, porous coating of fluorinated ethylene propylene. It has a thickness of about 0.02 mm and a width that is greater than the length of the endoprosthesis 11 intended to be constrained. Four layers of this film 26 are sequentially wrapped about the surface of a stainless steel mandrel having a diameter equal to the outside diameter of the compacted endoprosthesis 11 intended to be constrained, with the circumferential wrapping of the mandrel accomplished in the machine direction of the film. A line of perforations 14 are provided for the full length of the tube through the thickness of this film 26 using a laser, after which the helical wrapping is completed with a fifth layer of the film. The resulting five layer tube, still on the mandrel, is restrained against the surface of the mandrel at the tube ends and placed into an oven set at a temperature of about 320° C. for about five minutes, after which it is removed from the oven and allowed to cool. The end restraints are removed and the five layer tube is then removed from the mandrel and trimmed to the desired length equivalent to the length of the endoprosthesis 11. The resulting constraining sheath 13 is ready to be fitted about the exterior surface of compacted endoprosthesis 11. The endoprosthesis may be compacted by drawing it through a funnel with the aid of a fiber temporarily attached to the endoprosthesis. The endprosthesis is drawn through the funnel into a length of metal or plastic tubing of constant diameter and finally into the constraining sheath.

Figure 3:
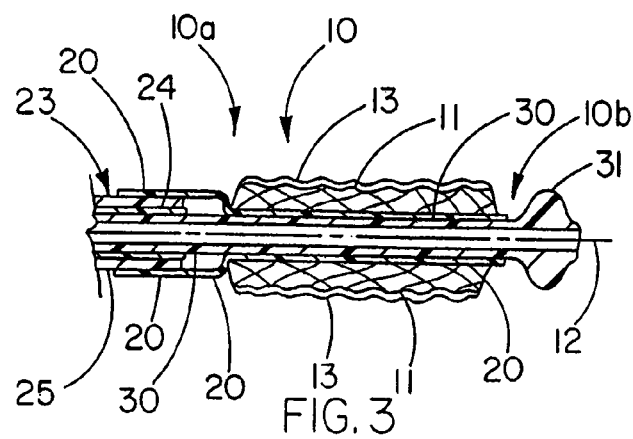
FIG. 3 is a longitudinal cross section of a compacted and constrained endoprosthesis describing a preferred embodiment of the system of the present invention.

FIG. 3 is a longitudinal cross section of a preferred embodiment wherein a separate intermediate sheath 20 is affixed to the distal end of a delivery catheter tube 23. The delivery catheter tube 23 preferably is a length of the composite tubing described above having the PTFE lining within a wire-reinforced polyamide jacket. The inside diameter of this tubing is such that it provides a slight clearance for the outside diameter of the inner tube 30. The PTFE liner of both tubes allows for smooth axial operation of other components (tubes or wires) within the lumen of either tube.

Intermediate sheath 20 comprises a length of heat shrinkable PET tubing of about 0.03 mm thickness (Advanced Polymers Inc., Salem N.H.), fitted over the distal end of the delivery catheter tube 23, and joined to that tube with cyanoacrylate adhesive. After the adhesive has set, tension and heat are applied to the length of thin PET tubing to cause it to shrink in diameter in an amount to allow it to fit snugly over the outer surface of the inner tube 30. An approximately 5 mm long length of the PET tubing is left unshrunk to accommodate at least a portion of the protrusion 31 when it is subsequently drawn through the endoprosthesis 11. The length of the intermediate sheath 20 is cut off transversely to a length that allows it to extend beyond the distal end of endoprosthesis 11. Preferably, the full length of inner sheath 20 extending beyond the end delivery catheter tube 23 is slit in a direction parallel to longitudinal axis 12, forming intermediate sheath split 21 (FIG. 2B). Compacted endoprosthesis 11 is fitted around the slit intermediate sheath 20, and protrusion 31 is then fitted about the distal end of inner tube 30 as previously described.

Figure 4A:
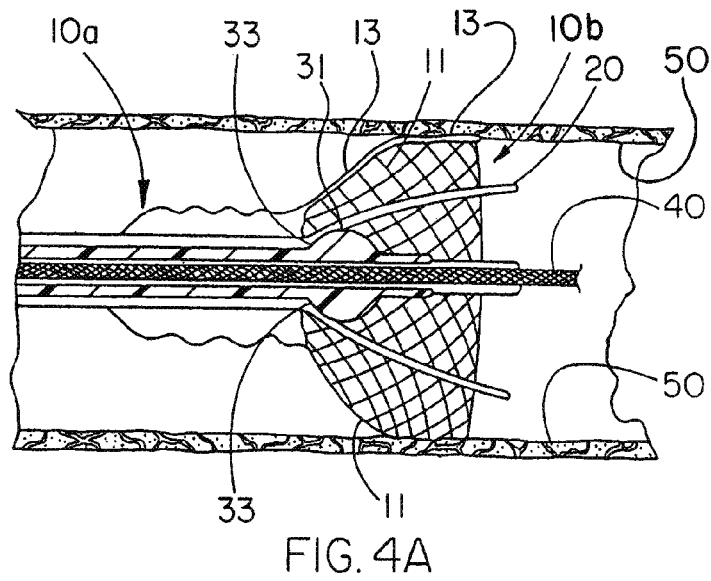
FIG. 4A is a longitudinal cross section of the endoprosthesis being deployed within a body conduit.
Figure 4B:
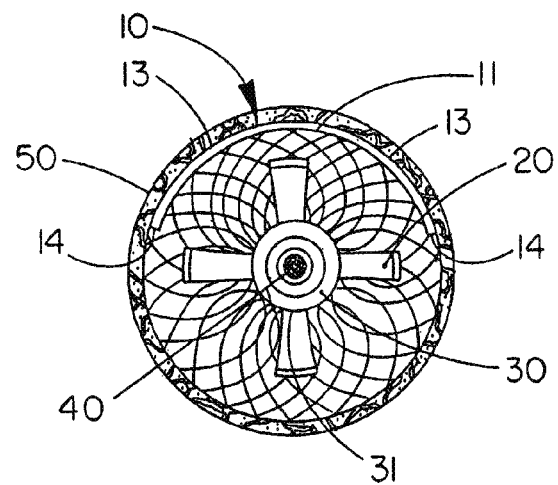
FIG. 4B is an end view of endoprosthesis deployment depicted in FIG. 4A.

FIG. 4A is a longitudinal cross section of the endoprosthesis 11 being deployed within a body conduit 50; FIG. 4B is an end view looking in a proximal direction of this deployment. Protrusion 31 is moved axially through intermediate sheath 20 and prosthesis 11 via tension applied to intermediate sheath 20. Intermediate sheath 20 is preferably the distal end of a tubular catheter shaft which supplies resistance compressively to the inner tube 30 and protrusion 31 (affixed to the inner tube 30) when those components are pulled axially through the endoprosthesis in a proximal direction. The mechanical advantage offered by inclined plane 33 on the leading edge or proximal side of protrusion 31, is utilized to apply a radial force to intermediate sheath 20, thereby causing disruption of the intermediate sheath 20. This radial force is at first resisted compressively by intermediate sheath 20, and quickly results in disruption of intermediate sheath 20, thereby initiating deployment of the self-expanding endoprosthesis 11. The expansion of endoprosthesis 11 progresses axially toward the proximal end 10a of the system 10.

The embodiment described in FIGS. 4A and 4B is that of FIG. 2D, wherein intermediate sheath is provided with multiple splits 21 along its length, in this instance 4 parallel and equally spaced splits. The end view of FIG. 4B shows the separation of these splits as the deployment progresses toward the proximal end of the system.

FIGS. 5A and 5C-5H are longitudinal cross sectional views of the inner tube 30 showing various embodiments of protrusion 31. These show that protrusion 31 may take any of various forms and are intended as exemplary and are not therefore limiting. The fundamental requirement is that the maximum diameter 32 of the protrusion 31 (taken perpendicular to the longitudinal axis 12) is larger than the inside diameter 22 of intermediate sheath 20, necessary to enable the protrusion 31 to disrupt the intermediate sheath 20.

FIG. 5A describes an embodiment wherein the protrusion 31 is fundamentally spherical in shape. However, as shown by the embodiment described in the end view of FIG. 5B, it is apparent that the protrusion is not required to be symmetrical in transverse cross section. As shown in FIG. 5B, the protrusion 31 may optionally be eccentric, having a maximum diameter 32 that is larger than a diameter taken through the longitudinal axis normal to the maximum diameter. The protrusion 31 must have a maximum diameter 32 that is larger than the inside diameter 22 of intermediate sheath 20, and is thereby capable of disrupting intermediate sheath 20 when an axial force is applied to the protrusion 31 to cause it to move axially against and/or through intermediate sheath 20 and endoprosthesis 11.

FIG. 5C is a longitudinal cross-section of the protrusion of FIG. 1, wherein the protrusion is similar to the round shape of FIG. 5A, but is provided with a more pronounced inclined plane 33, wherein the protrusion 31 merges with the inner tube in a less perpendicular fashion in order to reduce the axial force required to initiate disruption of the intermediate sheath 20 and cause expansion of the endoprosthesis 11.

FIGS. 5D and 5E are longitudinal cross-sections of alternative embodiments of protrusion 31.

FIG. 5F is a longitudinal cross-section of an alternative embodiment of protrusion 31 and inner tube 30, wherein the protrusion is enlargable such as in axial compression of the braided tubular form shown. Application of tension to a guidewire used within the lumen of the tubular braid (guidewire omitted from FIG. 5F for clarity) can be utilized to create the protrusion 31. By pre-forming the protrusion at the desired site in the length of braided wire, the location of the protrusion (along the length of the braided wire) and its maximum diameter can be pre-determined. In an alternative of this embodiment, the braided tubular form can be of length about equal to or slightly greater than the length of the constrained endoprosthesis. The entire length of this braided tubular form (i.e., the entire length of the intermediate sheath) can be caused to increase in diameter in a relatively uniform fashion when axial compression is applied to the braided tubular form by an elongate actuation member (e.g., inner tube 30) within the tubular braided wire.

FIG. 5G is a longitudinal cross-section of the protrusion 31, wherein the protrusion is an enlargeable, inflatable member. In another embodiment described by the longitudinal cross-section of FIG. 5H, the protrusion of FIG. 1, the protrusion is made up of a material dissolvable in body fluids.

Figure 6A:
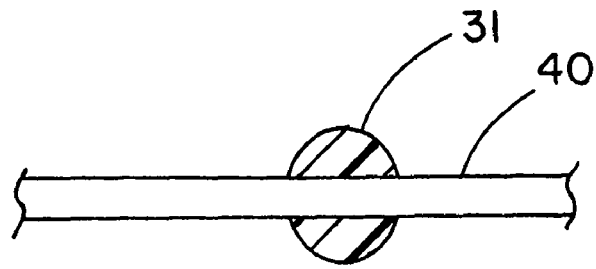
FIG. 6A is a longitudinal cross-section of the protrusion of FIG. 1, wherein the protrusion is attached to a guide wire.
Figure 6B:
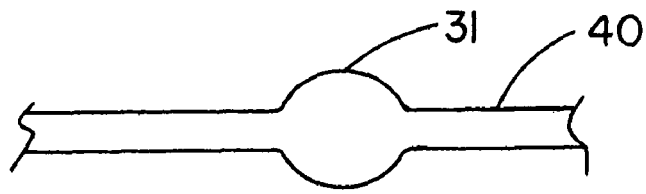
FIG. 6B is a longitudinal cross-section of the protrusion of FIG. 1, wherein the protrusion is integral to a guide wire.
Figure 6C:
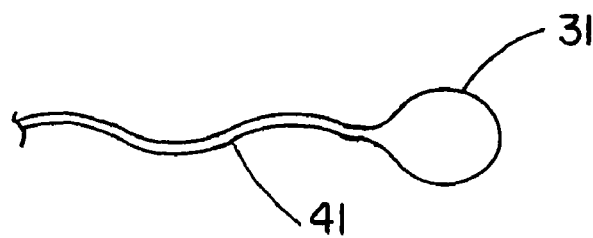
FIG. 6C is a longitudinal cross-section of the protrusion of FIG. 1, wherein the protrusion is attached to an elongate tensile member, such as a fiber, strand or wire.

FIGS. 6A and 6B are longitudinal cross-sections that show, respectively, that protrusion 31 may be attached to, or made integral with a guide wire 40, or other forms of elongate tensile members such as wires of other types, cables, strands, etc. FIG. 6C is a longitudinal cross-section indicating that protrusion 31 may be attached to the very end of an elongate tensile member if appropriate for particular applications.

Figure 7A:
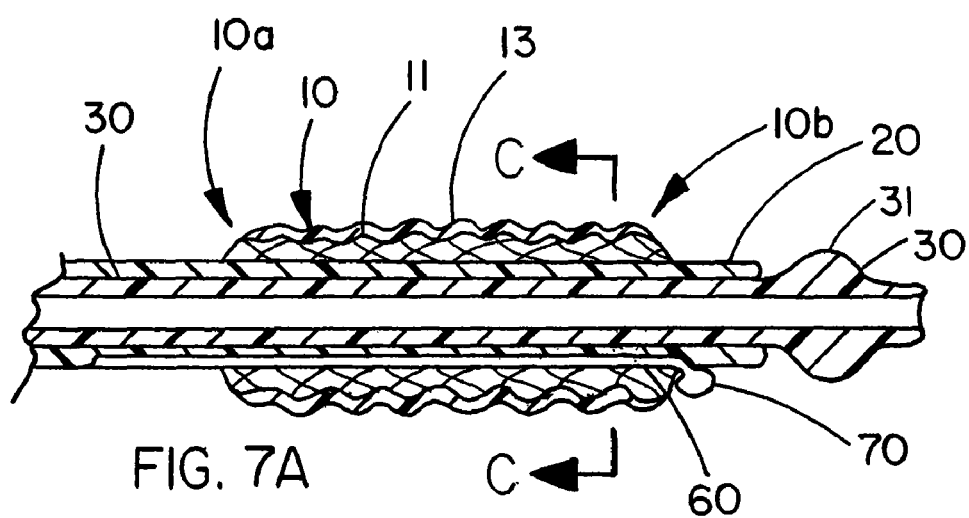
FIG. 7A is a longitudinal cross section of a compacted and constrained endoprosthesis incorporating a tether element with an enlargement at the distal end of the tether element, intended to prevent unintentional axial movement of the endoprosthesis.

FIG. 7A is a longitudinal cross section of a compacted and constrained endoprosthesis incorporating a tether element 60 having enlargement 70 at the distal end of the tether element 60, intended to prevent unintentional axial movement of the endoprosthesis. Enlargement 70 aids in holding the various components in the desired axial relationship until it is desired to actually expand and deploy endoprosthesis 11 by the use of relative tension applied to the inner tube 30 and protrusion 31.

Figure 7B:
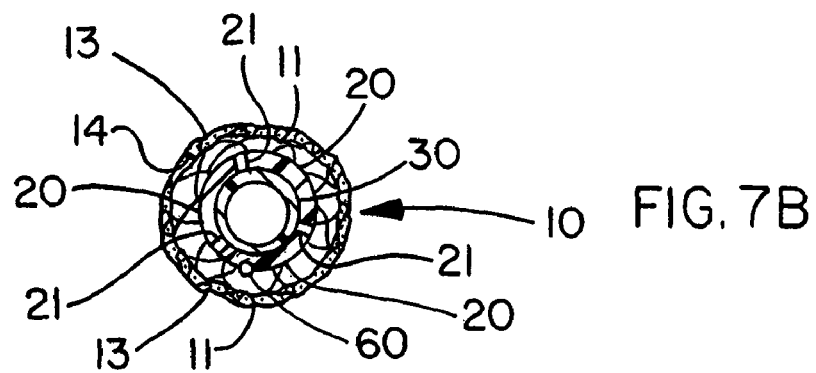
FIG. 7B is a transverse cross-section taken at section C-C of FIG. 7 describing the tether element.

FIG. 7B is a transverse cross-section taken at section C-C of FIG. 7A describing the tether element.

Figure 8A:
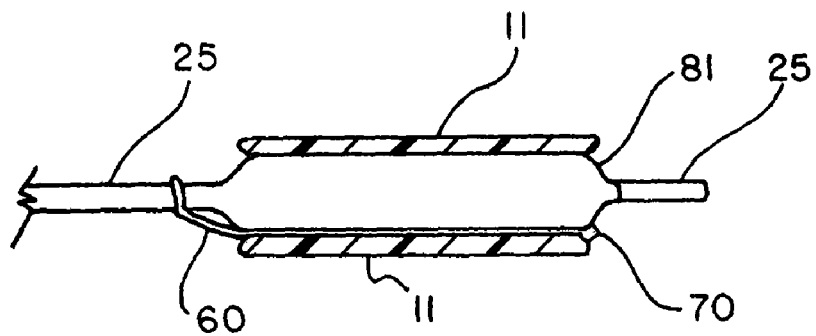
FIGS. 8A-8C are longitudinal cross sections describing alternative embodiments of the tether element.
Figure 8B:
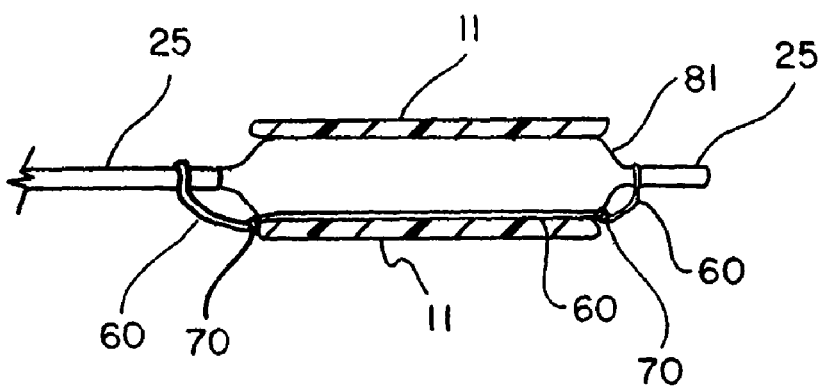

FIGS. 8A and 8B are longitudinal cross sections describing alternative tethers 60 wherein the tether 60 is used to secure an endoprosthesis 11 to another device such as a delivery catheter 25. One or both ends of tether 60 are secured to delivery catheter 25. One or more enlargements 70 are provided as restraints resisting any inadvertent displacement between the catheter 25 and the endoprosthesis 11. Tether 60 is held captive between endoprosthesis 11 and balloon 81. When balloon 81 is inflated to expand and deploy endoprosthesis 11, the tether 60 remains captive. When balloon 81 is subsequently deflated, tether 61 is freed from endoprosthesis 11 and may be withdrawn from the body conduit into which the endoprosthesis 11 has been inserted along with catheter 25 and attached balloon 81.

Figure 8C:
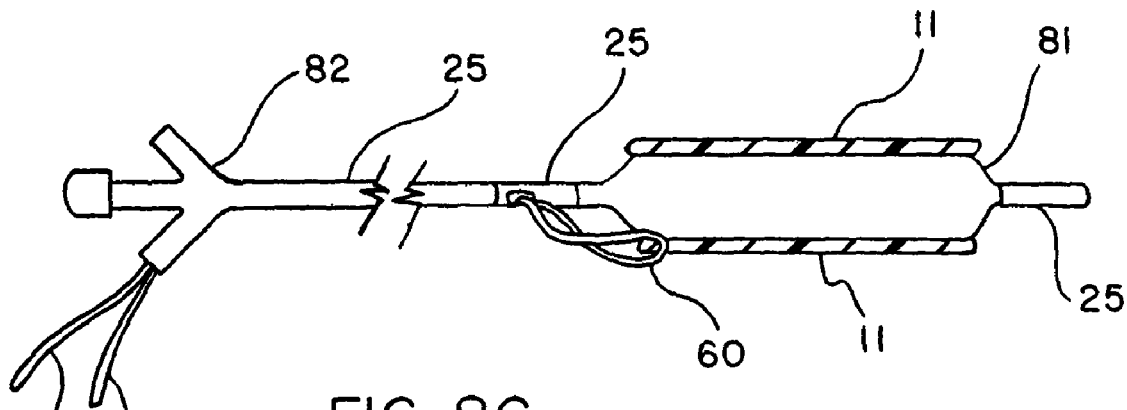

FIG. 8C is a longitudinal cross section of a tether 60 passed through an endoprosthesis 11 that is compacted onto a catheter balloon 81. FIG. 8C includes a side view of a hub 82 at the proximal end of the system, showing the tether 60 having both ends extending out of hub 82 wherein following inflation of balloon 81 and deployment of endoprosthesis 11, tether 60 may be withdrawn by pulling on one end.

Figure 9:
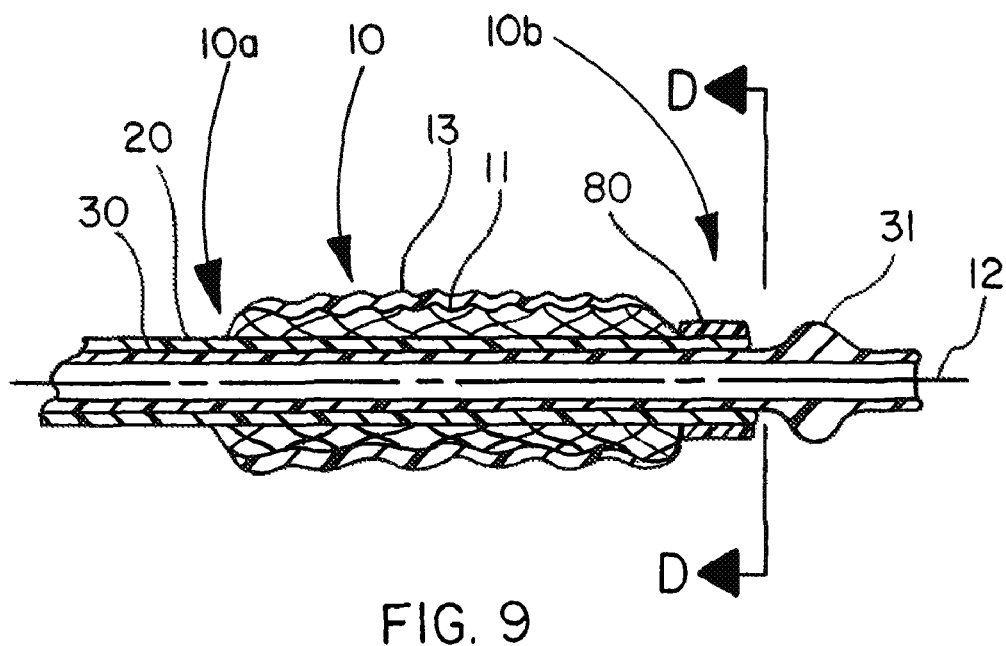
FIG. 9 is a longitudinal cross section of a compacted and constrained endoprosthesis incorporating a distensible collar positioned at the end of the endoprosthesis and intended to prevent unintentional axial movement of the endoprosthesis

FIG. 9 is a longitudinal cross section of a compacted and constrained endoprosthesis 11 incorporating a distensible collar 80 preferably positioned at the distal end of the endoprosthesis 11, intended to prevent unintentional axial movement of endoprosthesis 11. Collar 80 may be a separate component affixed to the exterior of intermediate sheath 20 at the distal end thereof, immediately proximal to protrusion 31, or may be made to be integral to the intermediate sheath 20. It is also apparent that the collar 80 may simply be of the form of any sort of enlargement in the diameter of the distal end of the intermediate sheath 20 that interferes with axial movement of the endoprosthesis 11 and thus prevents an unintentional movement of the endoprosthesis. As such, the enlargement is not required to extend entirely around the circumference of the distal end of intermediate sheath 20 in the fashion of collar 80. Such an enlargement may be integral with the distal end of intermediate sheath 20 or separately affixed. In an alternative, either the collar or another form of enlargement may be positioned beneath the endoprosthesis anywhere within the length of the endoprosthesis, thereby making difficult any unintended movement of the endoprosthesis with respect to the elongate tensile member 30.

Figure 10:
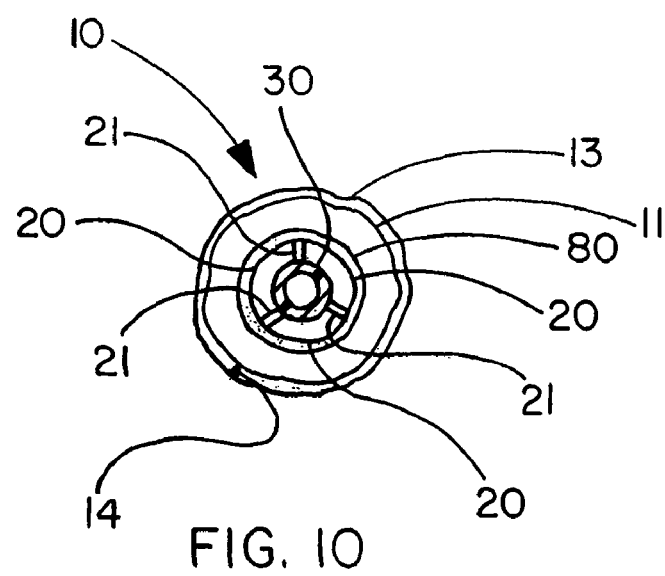
FIG. 10 is a transverse cross sectional view taken at section D-D of FIG. 9, describing the distensible collar element.

FIG. 10 is a transverse cross section taken at section D-D of FIG. 9, describing the distensible collar 80.

Figure 11A:
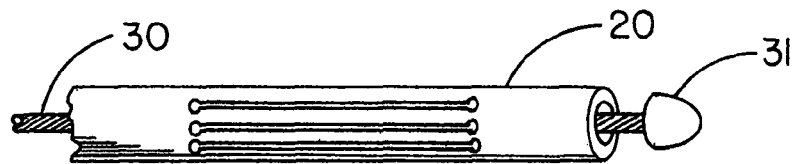
FIGS. 11A-11C, 12A and 12B are perspective views describing alternative embodiments of the present invention, primarily with regard to variations of the substantially tubular, intermediate sheath.
Figure 11B:
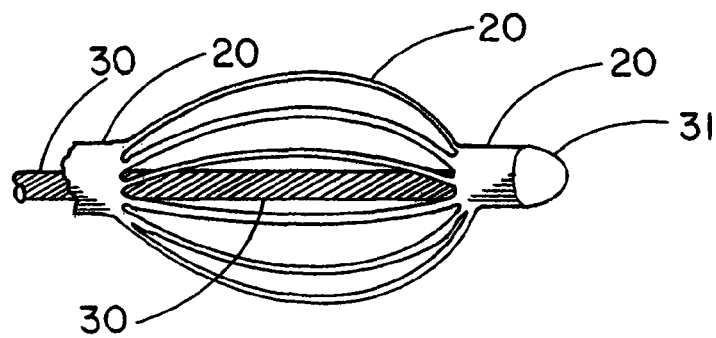
Figure 11C:
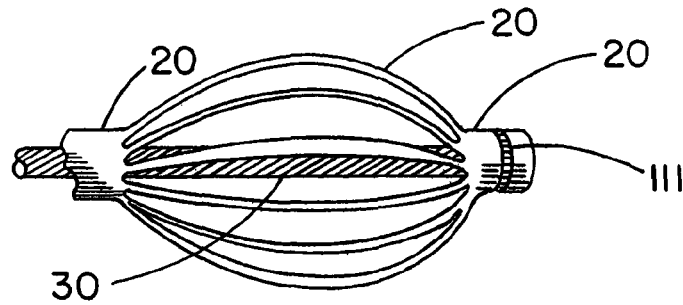

FIGS. 11A and 11B are perspective views of an alternative embodiment of the present invention wherein the substantially tubular sheath 20 contains multiple parallel splits adjacent to its distal end that do not extend entirely to the end. As shown by FIG. 11B, this form of the intermediate sheath 20 would increase in diameter when the protrusion 31 is pulled against its distal end by elongate actuation member 30, thereby exerting a radially outward directed force against endoprosthesis 11 (not shown) and initiating expansion and deployment of the endoprosthesis. In an alternative embodiment shown by FIG. 11C, protrusion 31 is no longer required and the distal end of the substantially tubular sheath is secured to the distal end of the elongate actuation member 30, whereby axial movement of the elongate tensile member 30 with respect to the substantially tubular sheath 20 results in a compressive force applied to the substantially tubular sheath 20, causing it to deform outwardly and exert a radially outward force against the endoprosthesis 11 (not shown) to initiate expansion and deployment of the endoprosthesis. The distal end of elongate actuation member 30 may be secured to the distal end of the substantially tubular sheath 20 by any of various means including compression ring 111, or by the use of an adhesive, welding, etc.

Figure 12A:
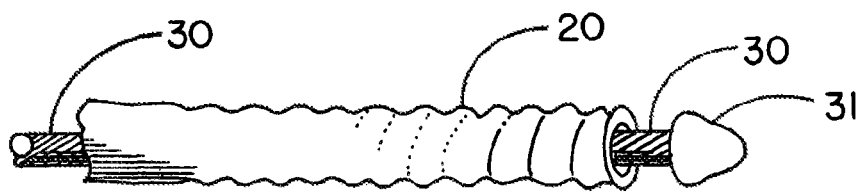
Figure 12B:
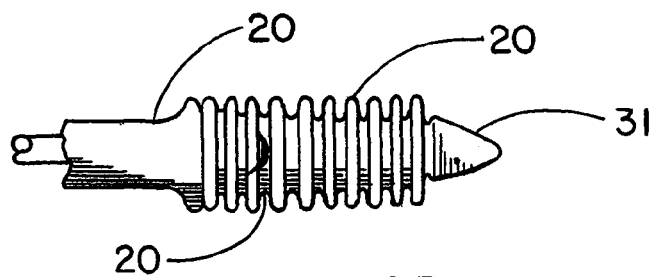

FIGS. 12A and 12B are alternative embodiments to those of FIGS. 11A and 11B wherein the substantially tubular sheath 20 is made to increase in diameter in a corrugated or accordion-fashion when protrusion 31 is moved axially against the substantially tubular sheath 20 by the application of tension to the elongate actuation member 30. As with the embodiment of FIG. 11C, this can also be accomplished without requiring a protrusion 31 by securing the distal end of the substantially tubular sheath 20 to the distal end of the elongate actuation member 30.

While the principles of the invention have been made clear in the illustrative embodiments set forth herein, it will be obvious to those skilled in the art to make various modifications to the structure, arrangement, proportion, elements, materials and components used in the practice of the invention. For example, the protrusion may be fitted at the proximal end of the system and moved axially in a distal direction to initiate endoprosthesis expansion in a proximal-to-distal direction. To the extent that these various modifications do not depart from the spirit and scope of the appended claims, they are intended to be encompassed therein.

The invention claimed is:

1. An endoluminal expansion system comprising:
    a) an elongate actuation member having a distal end;
    b) a substantially tubular sheath mounted coaxially about the elongate actuation member, said substantially tubular sheath having proximal and distal ends and a length extending between those ends, and further having multiple parallel slots extending along less than the entire length of the substantially tubular sheath, said elongate actuation member being axially movable with respect to the substantially tubular sheath, wherein the distal end of the substantially tubular sheath is secured to the distal end of the elongate actuation member; and
    c) an expandable endoprosthesis affixed coaxially about the substantially tubular sheath;
    wherein the application of tension to the elongate actuation member applies compression to the substantially tubular sheath whereby a radially outward force is applied to the expandable endoprosthesis by the substantially tubular sheath.

2. An endoluminal expansion system according to claim 1 wherein said endoprosthesis is a self-expanding endoprosthesis and is contained within a disruptable constraining sheath.

3. An endoluminal expansion system according to claim 2 wherein said constraining sheath is disruptable via a row of perforations.

4. An endoluminal expansion system according to claim 2 wherein said constraining sheath comprises porous expanded polytetrafluoroethylene.

5. An endoluminal expansion system according to claim 2 wherein said constraining sheath comprises a delicate constraining sheath contained within a packaging sheath that is removable prior to insertion of the endoluminal expansion system into a body conduit.

6. An endoluminal expansion system according to claim 1 wherein said elongate actuation member comprises a tube.

7. An endoluminal expansion system according to claim 1 wherein said elongate actuation member comprises an elongate tensile member.

8. An endoluminal expansion system according to claim 7 wherein said elongate tensile member comprises a guidewire.

9. An endoluminal expansion system according to claim 1 wherein said system incorporates a tether element.

10. An endoluminal expansion system according to claim 1 wherein the distal end of said substantially tubular sheath is secured to the distal end of the elongate actuation member by an enlargement secured to the distal end of the elongate actuation member.

11. An endoluminal expansion system according to claim 10 wherein said enlargement is a collar.

12. An endoluminal expansion system according to claim 1 wherein the application of compression to the substantially tubular sheath causes the substantially tubular sheath to assume a corrugated shape.

* * * * *